US009687172B2

(12) United States Patent
Bhat et al.

(10) Patent No.: US 9,687,172 B2
(45) Date of Patent: Jun. 27, 2017

(54) SYSTEM FOR MOTION CORRECTED MR DIFFUSION IMAGING

(75) Inventors: Himanshu Bhat, Cambridge, MA (US); Andre Jan Willem Van Der Kouwe, Woburn, MA (US); Matthew Dylan Tisdall, Somerville, MA (US); Keith Aaron Heberlein, Charlestown, MA (US)

(73) Assignees: National Institute of Health (NIH), The United States of America, U.S. Dept. of Health and Human Services (DHHS), Washington, DC (US); Siemens Healthcare GmbH, Erlangen (DE)

( * ) Notice: Subject to any disclaimer, the term of this patent is extended or adjusted under 35 U.S.C. 154(b) by 1408 days.

(21) Appl. No.: 13/527,706

(22) Filed: Jun. 20, 2012

(65) Prior Publication Data
US 2013/0187649 A1 Jul. 25, 2013

Related U.S. Application Data

(60) Provisional application No. 61/589,969, filed on Jan. 24, 2012.

(51) Int. Cl.
*A61B 5/055* (2006.01)
*G01R 33/563* (2006.01)
*G01R 33/567* (2006.01)

(52) U.S. Cl.
CPC .......... *A61B 5/055* (2013.01); *G01R 33/5676* (2013.01); *G01R 33/56341* (2013.01)

(58) Field of Classification Search
CPC .......... G01R 33/56341; G01R 33/5676; A61B 5/055
(Continued)

(56) References Cited

U.S. PATENT DOCUMENTS 5,353,794 A * 10/1994 Miyazaki ............. G01R 33/561
324/307
5,539,310 A * 7/1996 Basser ............. G01R 33/56341
324/307
(Continued)

FOREIGN PATENT DOCUMENTS

CN 1151858 A 6/1997
CN 1711481 A 12/2005
(Continued)

OTHER PUBLICATIONS

Chinese Office Action dated Jul. 27, 2015 in CN Application No. 201310026721.5, 14 pages (English translation attached).
(Continued)

*Primary Examiner* — Melissa Koval
*Assistant Examiner* — Sidmar Holloman

(57) ABSTRACT

A system determines motion correction data for use in diffusion MR imaging using an RF signal generator and magnetic field gradient generator which sequentially acquire in a single first direction through a volume, first and second slice sets individually comprising multiple individual diffusion image slices. The first set of slices and the second set of slices are spatially interleaved within the volume, by providing in acquiring the second slice set, a low flip angle RF pulse successively followed by a non-diffusion image data readout magnetic field gradient for acquisition of data representing a two dimensional (2D) non-diffusion image used for motion detection of the first slice set successively followed by, a first diffusion imaging RF pulse followed by a first diffusion imaging phase encoding magnetic field gradient for preparation for acquiring data representing a diffusion image slice of the second slice set.

13 Claims, 12 Drawing Sheets

(58) Field of Classification Search
USPC .......................................................... 324/309
See application file for complete search history.

(56) References Cited

U.S. PATENT DOCUMENTS

| | | | | |
|---|---|---|---|---|
| 5,545,993 | A * | 8/1996 | Taguchi | G01R 33/5676 324/307 |
| 5,786,692 | A * | 7/1998 | Maier | G01R 33/56341 324/307 |
| 6,320,377 | B1 * | 11/2001 | Miyazaki | A61B 5/055 324/306 |
| 6,614,226 | B2 * | 9/2003 | Wedeen | A61B 5/055 324/307 |
| 7,034,531 | B1 * | 4/2006 | Tuch | G01R 33/56341 324/309 |
| 7,078,897 | B2 * | 7/2006 | Yablonskiy | G01R 33/56341 324/306 |
| 9,488,710 | B2 * | 11/2016 | Boada | G01R 33/561 |
| 9,513,358 | B2 * | 12/2016 | Levin | G01R 33/56509 |
| 2004/0227510 | A1 * | 11/2004 | Rose | G01R 33/56518 324/309 |
| 2007/0249929 | A1 | 10/2007 | Jeong et al. | |
| 2008/0275329 | A1 | 11/2008 | Reeder et al. | |
| 2013/0158384 | A1 * | 6/2013 | Jeong | G01R 33/5615 600/410 |

FOREIGN PATENT DOCUMENTS

| | | |
|---|---|---|
| CN | 1961826 A | 5/2007 |
| CN | 102038502 A | 5/2011 |
| CN | 102188245 A | 9/2011 |
| WO | 2008135741 A1 | 11/2008 |
| WO | 2010116782 A1 | 10/2010 |

OTHER PUBLICATIONS

G.K. Rohde, et al., "Comprehensive Approach for Correction of Motion and Distortion in Diffusion—Weighted MRI", Magnetic Resonance in Medicine 51:103-114 (2004).

Murat Aksoy, et al., "Real-Time Optical Motion Correction for Diffusion Tensor Imaging", Magnetic Resonance in medicine 66:366-378 (2011).

M. Zaitsev, et al., "Magnetic resonance imaging of freely moving objects: Prospective real-time motion correction using an external optical motion tracking system", NeuroImage 31 (2006) 1038-1050.

Tobias Kober, et al., "Prospective and retrospective motion correction in diffusion magnetic resonance imaging of the human brain", NeuroImage 59 (2012) 389-398.

A.A. Alhamud, et al., "Implementation of real time motion correction in Diffusion Tensor Imaging", Proc. Intl. Soc. Mag. Reson. Med. 19 (2011).

Thomas Benner, et al., "Diffusion Imaging With Prospective Motion Correction and Reacquisition", Magnetic Resonance in Medicine, 66:154-167 (2011).

M.D. Tisdall, et al., "MPRAGE Using EPI Navigators for Prospective Motion Correction", Proc. Intl. Soc. Mag. Reson. Med. 17 (2009).

Stefan Thesen, et al., "Prospective Acquisition Correction for Head Motion With Image-Based Tracking for Real-Time fMRI", Magnetic Resonance in Medicine 44:457-465 (2000).

E.O. Stejskal and J. E. Tanner, "Spin Diffusion Measurements: Spin Echoes in the Presence of a Time Dependent Field Gradient", AIP The Journal of chemical Physics, 42, 288 (1965).

T.G. Reese, et al., "Reduction of Eddy-Current-Induced Distortion in Diffusion MRI Using a Twice-Refocused Spin Echo", Magnetic Resonance in Medicine 49:177-182 (2003).

\* cited by examiner

FIGURE 7
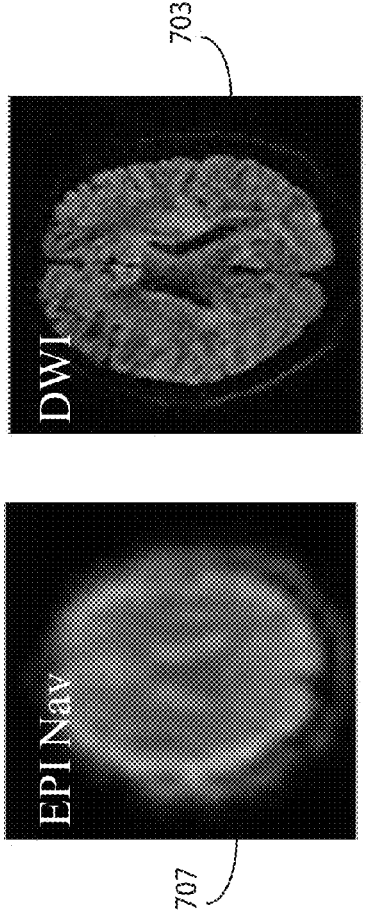
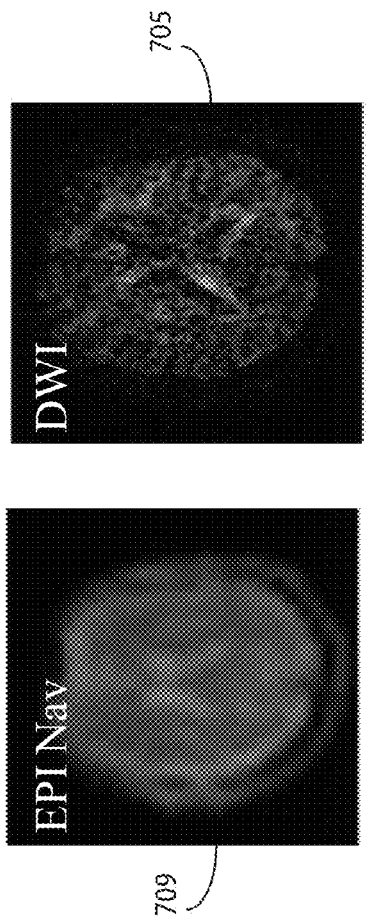

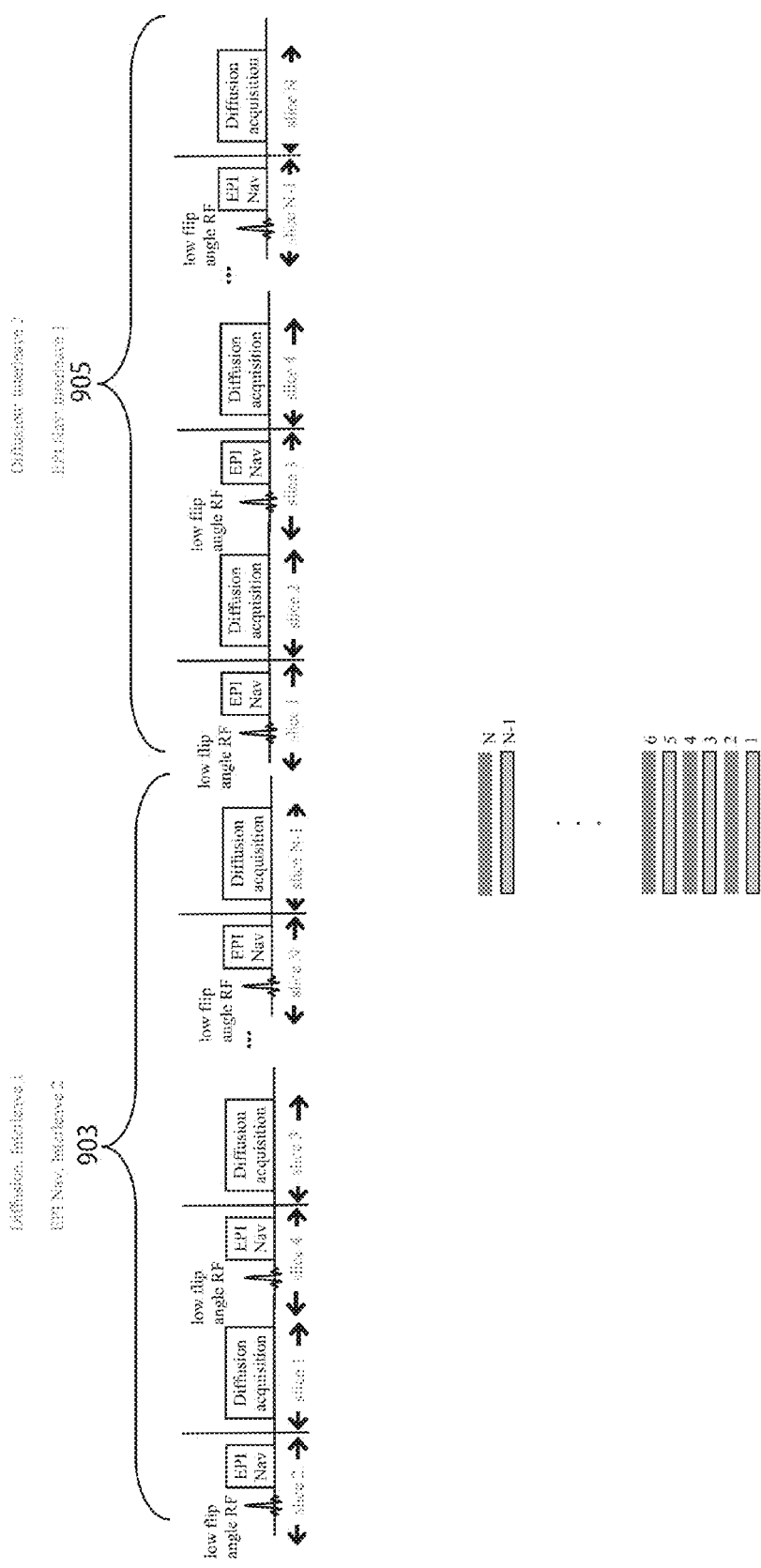

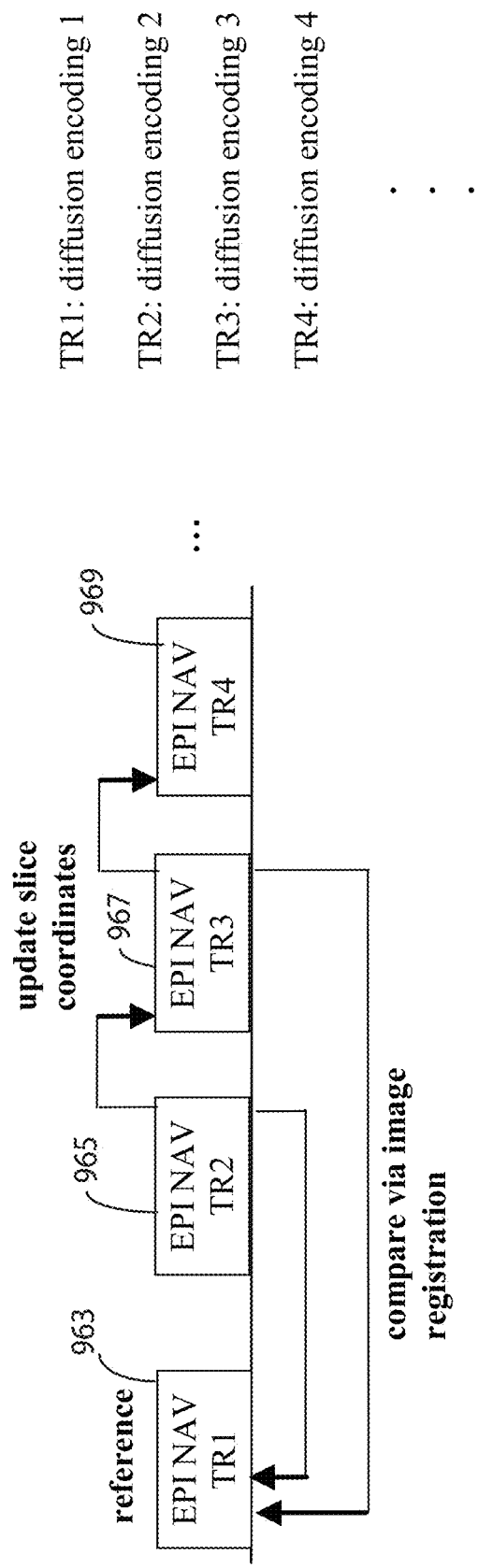

SYSTEM FOR MOTION CORRECTED MR DIFFUSION IMAGING

CROSS-REFERENCE TO RELATED APPLICATIONS

This application is a non-provisional of, and claims priority to, U.S. provisional patent application Ser. No. 61/589,969 by H. Bhat et al. filed on 24 Jan. 2012, incorporated herein by reference in its entirety.

FIELD OF THE INVENTION

This invention concerns a system for determining motion correction data for use in diffusion MR imaging of an anatomical volume.

BACKGROUND OF THE INVENTION

Diffusion MRI is a magnetic resonance imaging (MRI) method that produces in vivo images of biological tissues weighted with the local microstructural characteristics of water diffusion and is capable of showing connections between brain regions. In the presence of a magnetic field gradient, diffusion of water molecules leads to signal loss in MR images. The degree of signal loss depends on the characteristics of the diffusion, which in turn depends on tissue properties like structure, surrounding environment, physical state and pathology. The use of MR to probe such tissue properties based on water diffusion is called diffusion imaging. The magnetic field gradient used to probe tissue diffusion is called a diffusion gradient. The amount of signal loss during diffusion imaging depends on the dimensionless product: Db, where D is the diffusion coefficient in $mm^2/sec$, and b is a factor in $sec/mm^2$ which depends on the characteristics of the diffusion gradient. There are different methods of varying the magnitude and direction of the diffusion gradient to reconstruct a complete picture of the tissue properties. Such methods are called diffusion encoding methods. Diffusion imaging is usually performed with 2D multi-slice echo-planar imaging (EPI) based methods. The total scan time for such methods for human imaging can range from 1-30 minutes based on the type of diffusion encoding method used. For such long scans, bulk subject motion is a problem. In diffusion neuroimaging, problems occurring due to patient motion include, i) images acquired with different diffusion directions are misaligned, leading to erroneous calculation of diffusion parameters, and ii) images being acquired in a diffusion direction when motion occurs are susceptible to MR signal dropouts. Multiple known systems, both retrospective and prospective, attempt to address this problem with limited success. A system according to invention principles comprehensively addresses this problem and related problems.

SUMMARY OF THE INVENTION

A system determines motion correction data for use in diffusion MR imaging of an anatomical volume. An RF (Radio Frequency) signal generator generates RF excitation pulses in an anatomical region of interest and enables subsequent acquisition of associated RF echo data. A magnetic field gradient generator generates anatomical slice specific magnetic field gradients for phase encoding and readout RF data acquisition. In an interleaved embodiment, the RF signal generator and the gradient generator sequentially acquire in a single first direction through the volume, first and second slice sets individually comprising multiple individual diffusion image slices. The first set of slices and the second set of slices are spatially interleaved within the volume, by providing in acquiring the second slice set, a low flip angle RF pulse successively followed by a non-diffusion image data readout magnetic field gradient for acquisition of data representing a two dimensional (2D) non-diffusion image used for motion detection of the first slice set successively followed by, a first diffusion imaging RF pulse followed by a first diffusion imaging phase encoding magnetic field gradient for preparation for acquiring data representing a diffusion image slice of the second slice set.

In an integrated embodiment, the RF signal generator and the gradient generator acquire an individual diffusion image slice in a single first direction through the volume by providing a sequence comprising, a first diffusion imaging RF pulse, a non-diffusion image data readout magnetic field gradient for acquisition of data representing a two dimensional (2D) non-diffusion image used for motion detection and a first diffusion imaging phase encoding magnetic field gradient for magnetic preparation for acquiring data representing the individual diffusion image slice.

BRIEF DESCRIPTION OF THE DRAWINGS

FIG. 7 shows a sample EPI navigator image and a corresponding single direction diffusion weighted image (DWI) for the integrated prospective motion correction method (top row) and for the interleaved prospective motion correction method (bottom row), according to an embodiment of the invention.

FIGS. 9 and 10 illustrate image slice interleaving in an MR pulse sequence for interleaved prospective motion correction in diffusion MR imaging of an anatomical volume, according to an embodiment of the invention.

FIG. 11 illustrates use of EPI navigator image data for prospective motion correction in diffusion imaging, according to an embodiment of the invention.

DETAILED DESCRIPTION OF THE INVENTION

A system in one embodiment provides a rigid body prospective motion correction method for diffusion imaging using interleaved and integrated non-diffusion encoded low resolution Echo planar imaging (EPI) images as navigators. A navigator image determines position of an anatomical structure e.g. the diaphragm before image data acquisition of a desired region of interest. Navigator images are used to identify respiratory and other movement of the patient for synchronizing image data acquisition so that movement induced image blurring is minimized, for example. The system provides prospective motion correction for multi-slice single shot diffusion weighted EPI. The system provides prospective motion correction for 2D multislice diffusion imaging, by using non-diffusion encoded low resolution single shot EPI images as motion navigator (EPI Navigator images) during a diffusion scan. The system provides a prospective motion correction method for multi-slice single shot diffusion weighted EPI. Rigid body navigation is achieved using low resolution single shot EPI images without diffusion encoding as motion navigators during a diffusion scan.

Figure 1:
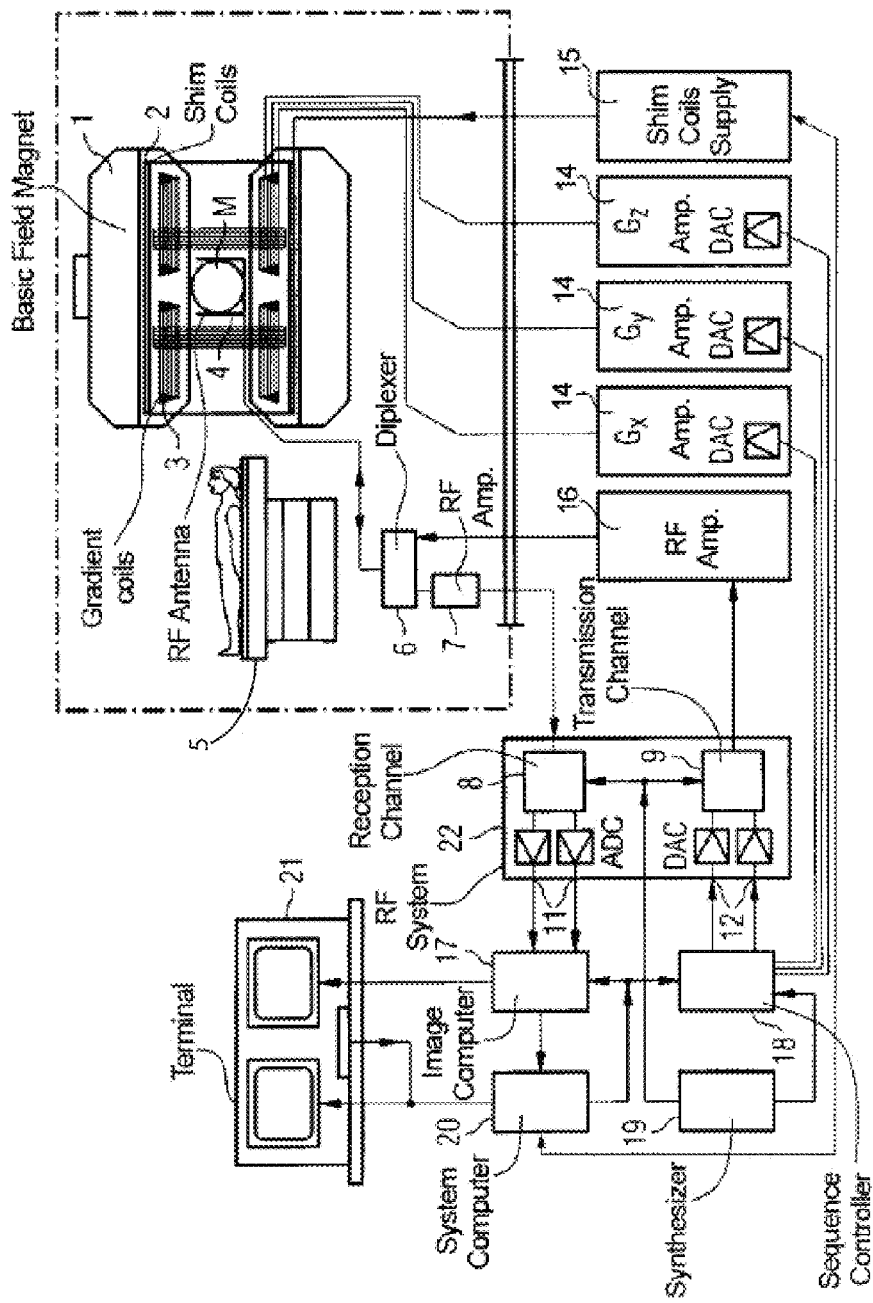
FIG. 1 shows a system for determining motion correction data for use in diffusion MR imaging of an anatomical volume, according to an embodiment of the invention.

FIG. 1 shows system 10 for determining motion correction data for use in diffusion MR imaging of an anatomical volume. In the basic field magnet 1, a cylinder-shaped gradient coil system comprising magnetic field gradient generator 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times. Homogeneity of the base magnetic field B0 is corrected using shim coils 2 electrically powered by shim coil supply 15.

Within the gradient field system 3, radio-frequency (RF) coils comprising RF (Radio Frequency) signal generator 4, are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In an interleaved embodiment, the RF (Radio Frequency) signal generator generates RF excitation pulses in an anatomical region of interest and enables subsequent acquisition of associated RF echo data. The magnetic field gradient generator generates anatomical slice specific magnetic field gradients for phase encoding and readout RF data acquisition. RF signal generator 4 and gradient generator 3 sequentially acquire in a single first direction through the volume, first and second slice sets individually comprising multiple individual diffusion image slices. The first set of slices and the second set of slices are spatially interleaved within the volume, by providing in acquiring the second slice set, a low flip angle RF pulse successively followed by a non-diffusion image data readout magnetic field gradient for acquisition of data representing a two dimensional (2D) non-diffusion image used for motion detection of the first slice set successively followed by, a first diffusion imaging RF pulse followed by a first diffusion imaging phase encoding magnetic field gradient for preparation for acquiring data representing a diffusion image slice of the second slice set.

In an integrated embodiment, RF (Radio Frequency) signal generator 4 generates RF excitation pulses in an anatomical region of interest and enables subsequent acquisition of associated RF echo data. Magnetic field gradient generator 3 generates anatomical slice specific magnetic field gradients for phase encoding and readout RF data acquisition. RF signal generator 4 and gradient generator 3 acquire an individual diffusion image slice in a single first direction through the volume by providing the sequence comprising, a first diffusion imaging RF pulse, a non-diffusion image data readout magnetic field gradient for acquisition of data representing a two dimensional (2D) non-diffusion image used for motion detection and a first diffusion imaging phase encoding magnetic field gradient for magnetic preparation for acquiring data representing the individual diffusion image slice.

Figure 2:
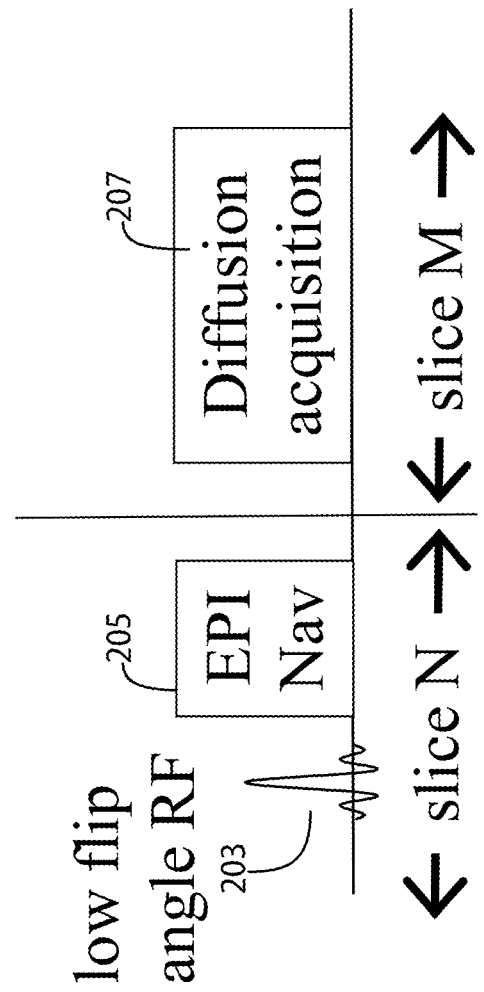
FIG. 2 shows basic MR pulse sequence components used for interleaved prospective motion correction in diffusion MR imaging of an anatomical volume, according to an embodiment of the invention.

FIG. 2 shows basic MR pulse sequence components used for interleaved prospective motion correction in diffusion MR imaging of an anatomical volume. A low pixel resolution 2D EPI Navigator (EPI NAV) non-diffusion image is acquired with a low flip angle RF excitation pulse 203 successively followed by a non-diffusion image data readout magnetic field gradient 205 for acquisition of data representing the low pixel resolution 2D EPI Navigator (EPI NAV) non-diffusion image used for motion detection of a first slice set. Successive diffusion acquisition block 207 includes RF and encoding and reading gradient pulses comprising a first diffusion imaging RF pulse followed by a diffusion imaging phase encoding magnetic field gradient for preparation for acquiring data representing a diffusion image slice of a second slice set. The diffusion acquisition may comprise different diffusion encoding methods like Stejskal-Tanner (Stejskal E O, Tanner J E. Spin Diffusion Measurements: Spin Echoes in the Presence of a Time-Dependent Field Gradient. Journal of Chemical Physics 1965; 42:288-292) and twice refocused (Reese T G, Heid O, Weisskoff R M, Wedeen V J. Reduction of eddy-current-induced distortion in diffusion MRI using a twice-refocused spin echo. Magn Reson Med 2003; 49(1): 177-182).

Figure 5:
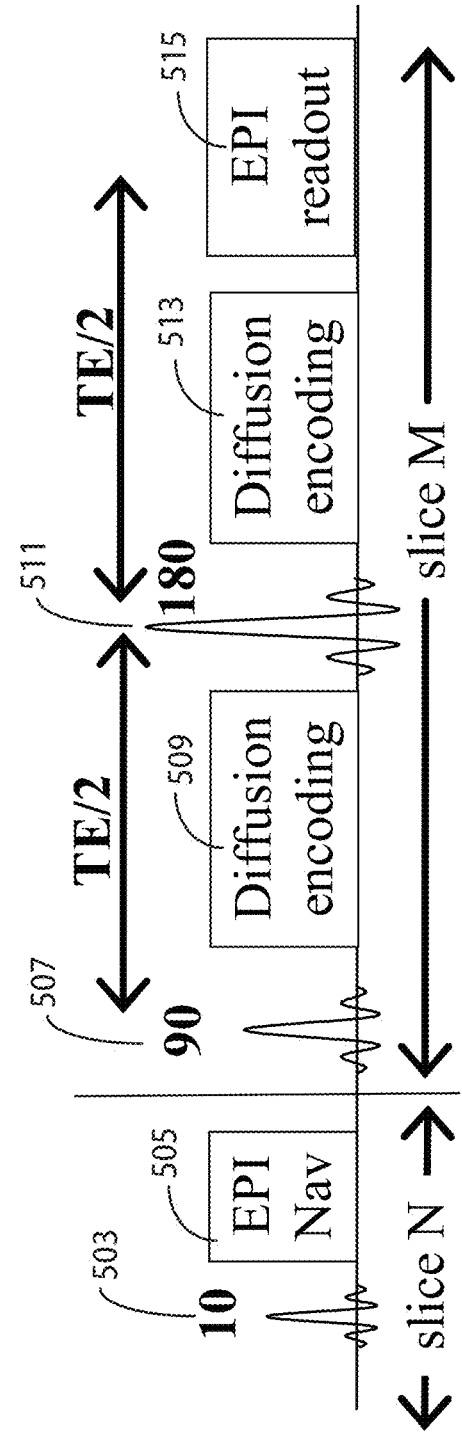
FIG. 5 shows an MR pulse sequence used for interleaved prospective motion correction in diffusion MR imaging of an anatomical volume, according to an embodiment of the invention.

FIG. 5 shows an MR pulse sequence used by system 10 (FIG. 1) for interleaved prospective motion correction in diffusion MR imaging of an anatomical volume. A low pixel resolution 2D EPI Navigator (EPI NAV) non-diffusion image is acquired with a low flip angle (e.g., 10 degree) RF excitation pulse 503 successively followed by a non-diffusion image data readout magnetic field gradient 505 for acquisition of data representing the low pixel resolution 2D EPI Navigator (EPI NAV) non-diffusion image used for motion detection of a first slice set (including slice N). Following gradient 505, the pulse sequence includes a 90 degree flip angle RF excitation pulse 507 and diffusion imaging phase encoding magnetic field gradient 509 successively followed by a 180 degree flip angle imaging RF pulse 511 followed by a second diffusion imaging phase encoding magnetic field gradient 513, followed by a diffusion image data readout magnetic field gradient 515 for acquisition of the data representing a diffusion image slice of a second slice set (including slice M). The diffusion and EPI Navigator acquisitions acquire prescribed slices during a total repetition time (TR$_{ALL}$) comprising multiple individual TR repetition times (between successive RF excitation pulses) for acquiring a predetermined total number of slices in a diffusion imaging direction using a particular diffusion encoding method. Diffusion and non-diffusion acquisitions to acquire slices may occur in an independent order.

Rigid body navigation is achieved using non diffusion encoded low resolution single shot EPI images as motion navigators (EPI Navigators) during a diffusion scan. Prior to acquiring slice M for diffusion, slice N is acquired with a low) (10°) flip angle for acquisition of EPI Navigator image data and the EPI Navigator and diffusion acquisitions are decoupled. A diffusion image series is acquired in 2 interleaves, slices M and N are adjacent in space, but TR/2 separated in time in a diffusion scan. For typical TRs of 7-9 sec such a low flip angle excitation results in negligible signal loss in the diffusion acquisition. For an interleaved method, an EPI Navigator acquisition is acquired in 10.5 ms per slice in an acquisition, for example. For a diffusion acquisition an optimized way to acquire EPI Navigator image data is used. When the diffusion acquisition is acquiring Interleave1, the EPI Navigator acquires Interleave2 and when the diffusion acquisition is acquiring Interleave2 the EPI Navigator acquires Interleave1 as illustrated in FIG. 9. This way the EPI Navigator and diffusion slices are TR$_{ALL}$/2 separated in time. This minimizes the interaction between the EPI Navigator and diffusion acquisitions and results in minimum signal attenuation in the diffusion scan due to the EPI Navigator scan.

FIGS. 9 and 10 show interleaved prospective motion correction imaging indicating interleaving between diffusion and EPI Navigator slices. FIG. 10 illustrates a single TR$_{ALL}$ of interleaved prospective motion correction imaging indicating interleaving between diffusion slices and EPI Navigator slices corresponding to the slices of the pulse sequence of FIG. 9. The diffusion image acquisition is usually acquired in two interleaves. Diffusion interleave 1 (of pulse sequence 903) comprises diffusion slices 1, 3, 5 . . . N–1 and Interleave 2 (of pulse sequence 905) comprises diffusion slices 2, 4, 6 . . . N.

FIG. 9 illustrates image slice interleaving in an MR pulse sequence for interleaved prospective motion correction in diffusion MR imaging of an anatomical volume. Pulse sequence portion 903 comprises diffusion imaging interleave 1 and 2D EPI Navigator (EPI NAV) non-diffusion image interleave 2 including diffusion image slices 1, 3, 5 . . . N–1 and EPI Navigator image slices 2, 4 . . . N. Pulse sequence portion 905 comprises diffusion imaging interleave 2 and 2D EPI Navigator (EPI NAV) non-diffusion image interleave 1 including diffusion image slices 2, 4 . . . N and EPI Navigator image slices 1, 3, 5 . . . N–1. The interleaved method maintains the original TE for the diffusion images, and results in no SNR change in the diffusion images. The interleaved prospective motion correction diffusion MR imaging method adds extra RF pulses into a sequence leading to a slight increase in Specific Absorption Rate (SAR) and uses an interleaving process so that the diffusion and EPI Navigator image acquisitions do not interfere with each other. The interleaved method provides motion estimates for volume registration.

Figure 3:
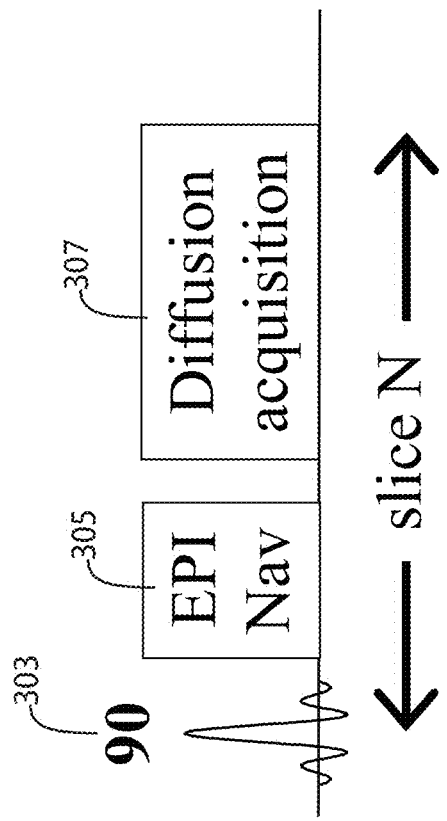
FIG. 3 shows basic MR pulse sequence components used for integrated prospective motion correction in diffusion MR imaging of an anatomical volume, according to an embodiment of the invention.

FIG. 3 shows basic MR pulse sequence components used for integrated prospective motion correction in diffusion MR imaging of an anatomical volume. Rigid body navigation is achieved using non diffusion encoded low resolution single shot EPI images as motion navigators (EPI Navigator) during a diffusion scan. Low pixel resolution 2D EPI Navigator (EPI NAV) non-diffusion image data is acquired with a 90 degree RF excitation pulse 303 successively followed by a non-diffusion image data readout magnetic field gradient 305 for acquisition of data representing the low pixel resolution 2D EPI Navigator (EPI NAV) non-diffusion image used for motion detection. Successive diffusion imaging phase encoding magnetic field gradient 307 magnetically prepares an imaging volume for acquiring data representing an individual diffusion image slice. The diffusion and EPI Navigator acquisitions acquire the same slice. The diffusion acquisition may comprise different diffusion encoding methods like the Stejskal-Tanner and twice refocused methods previously described. The Echo Time (TE) for diffusion imaging phase encoding magnetic field gradient 307 is adjusted to account for the additional EPI Navigator acquisition 305. This is done with use of an appropriate fill time selected in response to the type of diffusion encoding method used.

Figure 4:
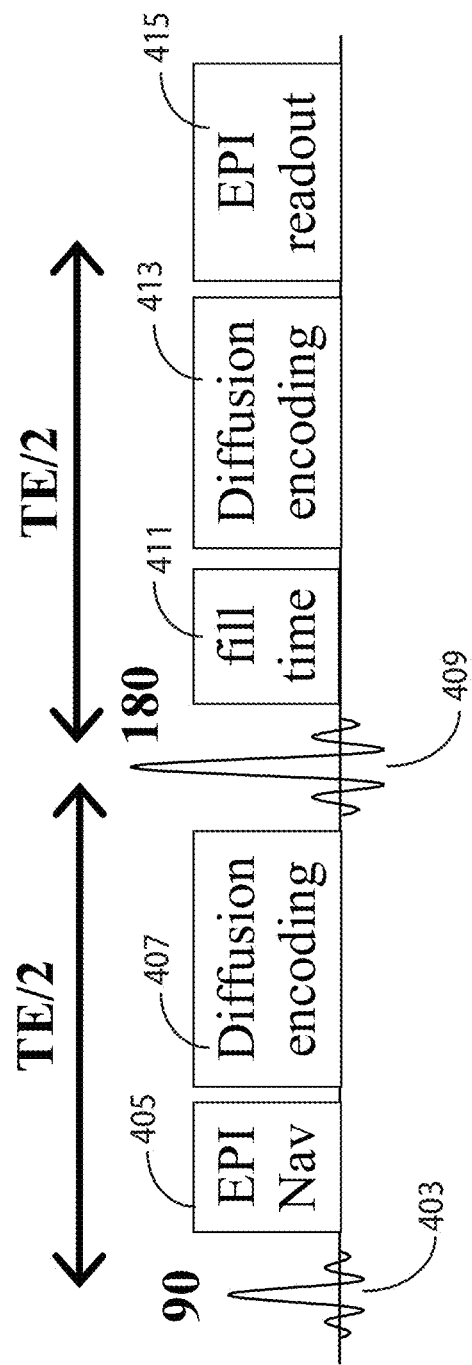
FIG. 4 shows an MR pulse sequence used for integrated prospective motion correction in diffusion MR imaging of an anatomical volume, according to an embodiment of the invention.

FIG. 4 shows an MR pulse sequence used for integrated prospective motion correction in diffusion MR imaging of an anatomical volume. Low pixel resolution 2D EPI Navigator (EPI NAV) non-diffusion image data is acquired with a 90 degree RF excitation pulse 403 successively followed by a non-diffusion image data readout magnetic field gradient 405 for acquisition of data representing the low pixel resolution 2D EPI Navigator (EPI NAV) non-diffusion image used for motion detection. Successive diffusion imaging phase encoding magnetic field gradient 407 magnetically prepares an imaging volume for acquiring data representing an individual diffusion image slice. Gradient 407 is successively followed by second diffusion imaging 180 degree RF pulse 409, second diffusion imaging phase encoding magnetic field gradient 413 and diffusion image data readout magnetic field gradient 415 for acquisition of data representing an individual diffusion image slice. Further, following second diffusion imaging RF pulse 409 and prior to second diffusion imaging phase encoding magnetic field gradient 413, a time delay (fill time) 411 is incorporated in the pulse sequence to correct an Echo Time (TE) value. Corresponding fill time 411 is inserted after 180° RF pulse 409 to maintain TE symmetry for a spin echo condition. In this study a 7.5 ms readout is used for EPI Navigator leading to a 15 ms increase in TE per slice. The integrated prospective motion correction diffusion MR imaging performed using the pulse sequences of FIGS. 3 and 4 involve an increase in TE in acquiring the diffusion images, which can lead to a SNR loss in the diffusion images. The integrated method provides slice specific motion estimates which are used in a slice to volume registration.

FIG. 11 illustrates use of EPI navigator image data for prospective motion correction in diffusion imaging. The use of low resolution non-diffusion encoded EPI Navigator images for prospective motion correction is substantially the same for both interleaved and integrated methods. The EPI Navigator image from a first repetition time (TR) 963 between successive RF excitation pulses is used as a reference image. The EPI Navigator images from subsequent TRs (e.g. 965, 967, 969) are compared with the reference images using image registration and the relative displacements of the images are calculated. A calculated displacement between a reference image and an image of a particular TR is used to update the slice coordinates for an image of a next TR such that motion of the subject is compensated.

Reference image for TR1 963 is compared with an image of TR2 965 to identify relative displacement and any relative displacement is used to update coordinates of an image of TR3 967, for example.

For both interleaved and integrated motion corrected diffusion imaging embodiments, over the course of a TR, a non diffusion encoded low resolution volume is created from EPI Navigator slices and used for prospective motion correction based on a 3DPACE (3D Prospective Motion Correction for fMRI) method which uses a 3D rigid body motion model. A first volume is used for determining a reference position by a known 3DPACE method. The EPI Navigator images are reconstructed using a real-time feedback framework on a scanner and an additional 50 ms delay is introduced at the end of each TR to enable real-time slice position updates for a next TR, based on motion estimates given by the 3DPACE method. In an exemplary test, 5 healthy volunteers were scanned using the first and second embodiment motion correction methods, and with a standard non motion corrected single shot EPI sequence. In order to evaluate the efficacy of system motion correction, subjects were deliberately instructed to follow a predefined motion protocol during three diffusion scans. Imaging was performed on a 3T scanner (Siemens MAGNETOM Skyra). Parameters for the diffusion scan were: Field of View (FOV): 220×220 mm$^2$, matrix: 128×128, b=1000 s/mm$^2$, 60 slices with 2 mm thickness, TE 73 ms, TR 7600/60 ms, 30 diffusion directions, bw=1396 Hz/pixel, GRAPPA factor=2. Parameters for the EPI Navigator scan were: FOV: 256×256 mm$^2$, matrix: 32×32, partial Fourier factor=0.66, b/w=4596 Hz/pixel, 60 slices with 2 mm thickness (same as diffusion acquisition). For the integrated scheme: TE 88 ms, TR 8610/60 ms. In order to demonstrate independence from the b-value, an additional diffusion scan with b=3000 s/mm$^2$ and 60 directions was collected in one volunteer.

Figure 6:
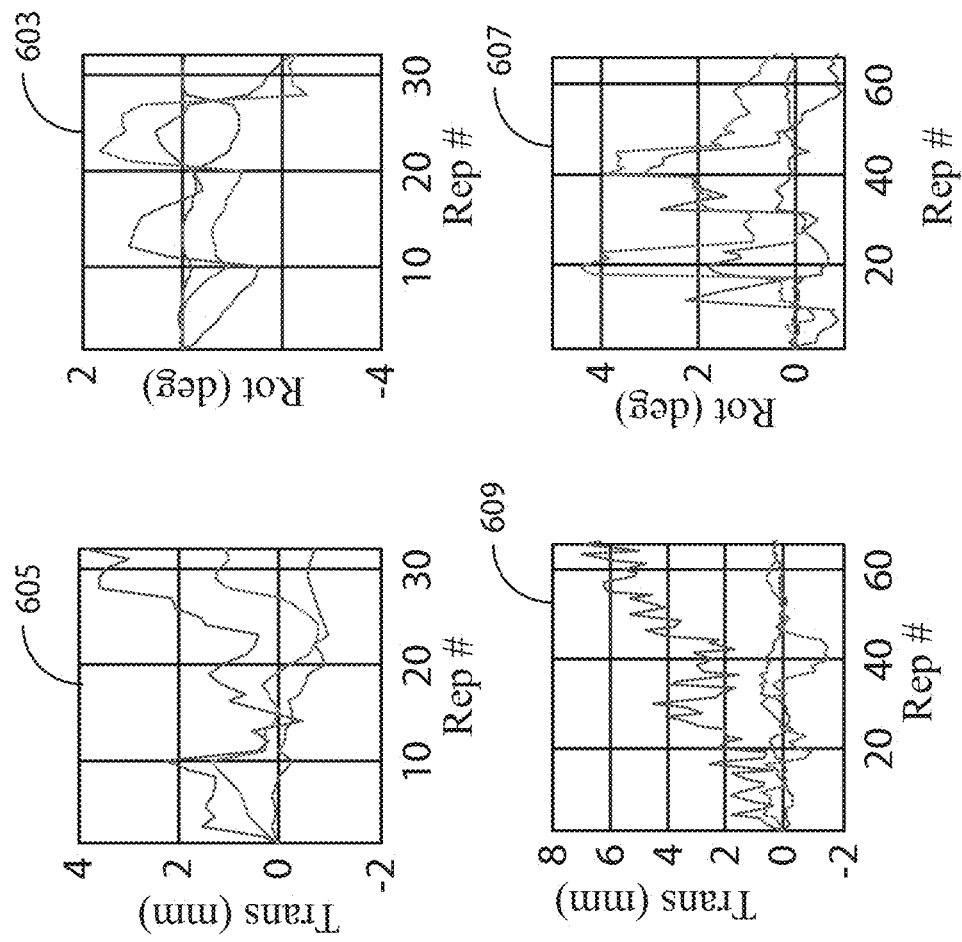
FIG. 6 shows rotations in degrees (Rot (deg)) and translations in mm (Trans (mm)) of image data detected with the EPI navigator method for an integrated method (top row) and interleaved method (bottom row) where a subject patient deliberately moved during the scans, according to an embodiment of the invention.

FIG. 6 shows detected image object rotations in degrees (Rot (deg)) 603, 607 due to patient motion and corresponding correction image data translations in mm (Trans (mm)) 605, 609) of image data detected with the EPI navigator method for an integrated method (top row) and interleaved method (bottom row) where a patient deliberately moved during the scans. The charts show 3 episodes of patient motion for 30 different diffusion directions (x-axis) top row and 60 different diffusion directions bottom row. FIG. 7 shows a sample EPI navigator image 707, and a corresponding single direction diffusion weighted image (DWI) 703 for the integrated prospective motion correction method (top row) and a sample EPI navigator image 709, and a corresponding single direction diffusion weighted image (DWI) 705 for the interleaved prospective motion correction method (bottom row). The integrated prospective motion correction method (top row) is performed for a first b-value (1000) and 30 diffusion directions and the interleaved prospective motion correction method (bottom row) is performed for a different second b-value (3000) and 64 diffusion directions. The EPI Navigator images are not diffusion encoded and have a good SNR even for a b-value of 3000 and give reliable motion estimates.

Figure 8B:
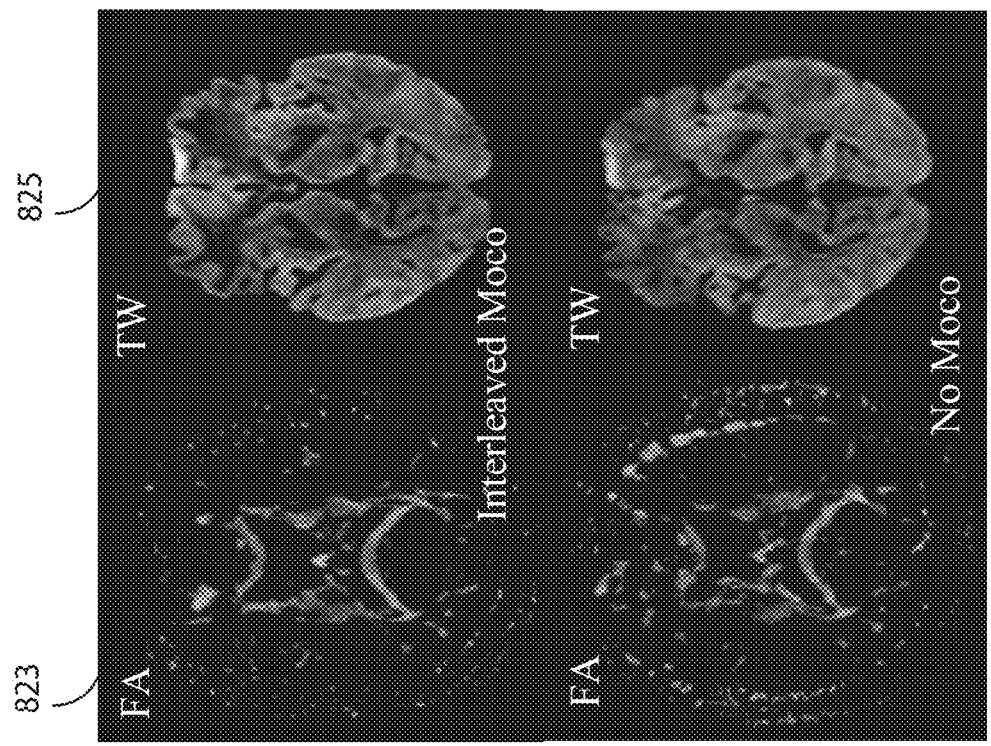
FIGS. 8A and 8B shows sample images for the integrated (top row FIG. 8A) and interleaved (top row, FIG. 8B) prospective motion correction embodiments, compared with a non motion corrected sequence (bottom row FIGS. 8A and 8B), according to an embodiment of the invention.
Figure 8A:
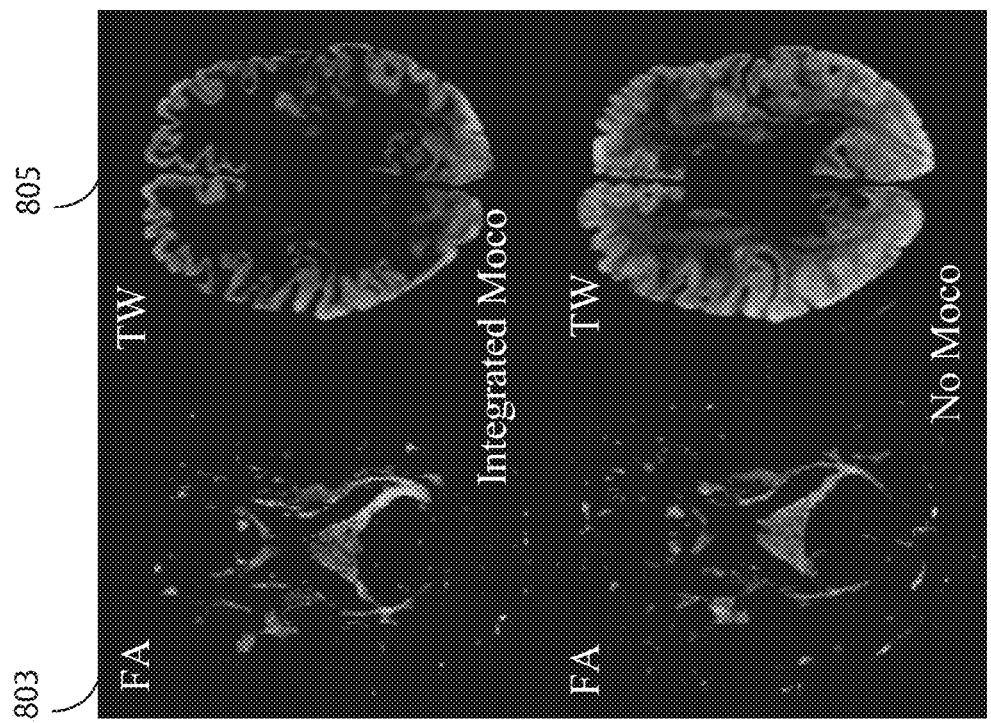

FIGS. 8A and 8B shows sample images 803, 805 for the integrated prospective motion correction embodiment (top row FIG. 8A) and sample images 823, 825 for the interleaved prospective motion correction embodiment (top row, FIG. 8B), compared with a non motion corrected sequence (bottom row FIGS. 8A and 8B). The improvement in trace weighted (TW) 805, 825 and fractional anisotropy (FA) 803, 823 images in both motion corrected sequences is apparent.

In addition, in order to evaluate the difference in signal level in the diffusion images between the corrected and uncorrected methods signal ratio in a white matter ROI was measured in the TW image. The integrated motion correction method had a 17.7% signal decrease (due to the increased TE); whereas the interleaved motion correction technique had a 0.57% signal decrease. The prospective motion correction embodiments advantageously improve diffusion neuroimaging and work independently of b-value used and do not need retrospective adjustment of a b-matrix. In the integrated embodiment, the TE and TR increase with corresponding signal decrease while the interleaved embodiment requires only a small (~10%) increase in minimum TR.

Figure 12:
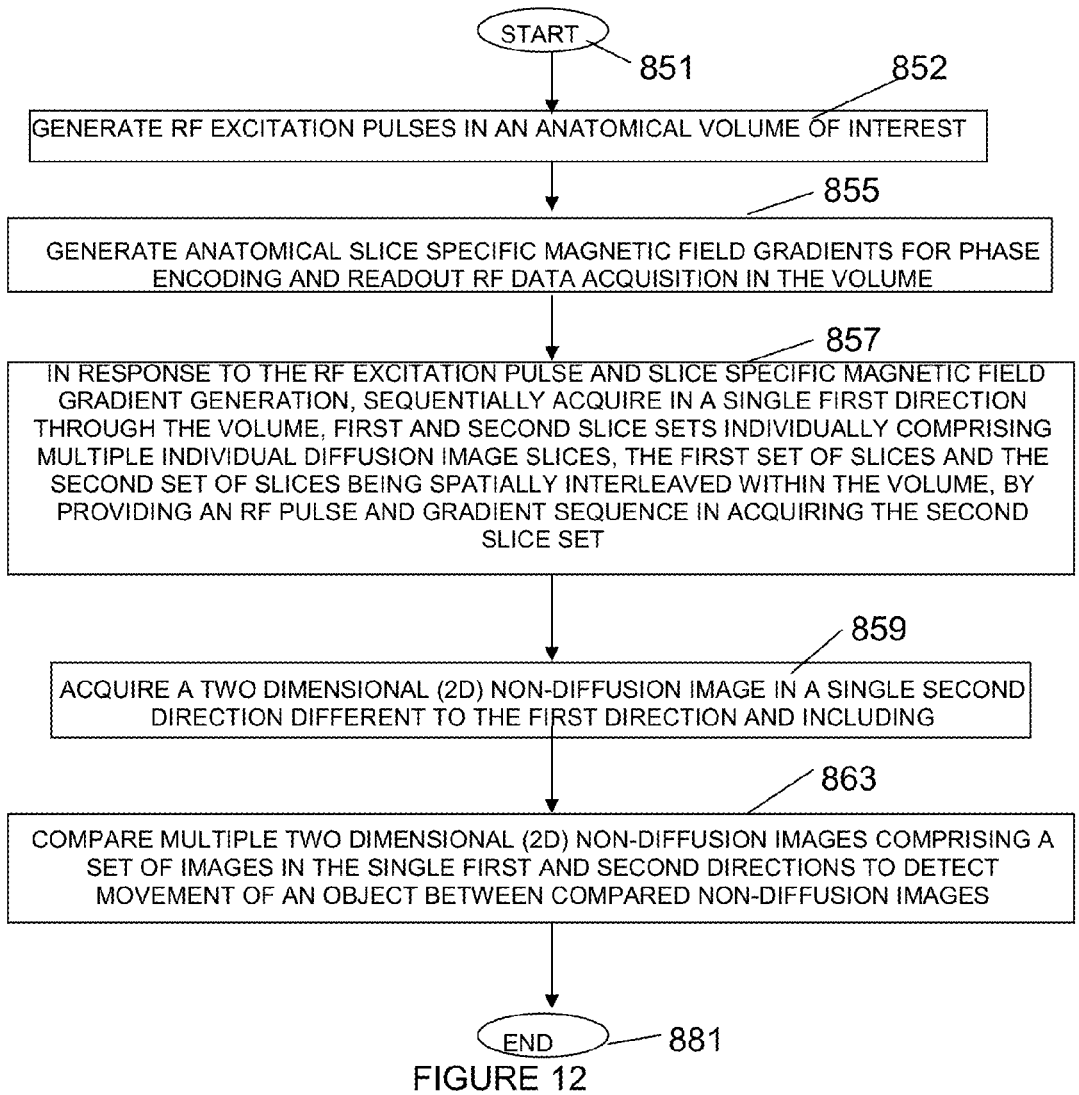
FIG. 12 shows a flowchart of a process performed by a system for determining motion correction data for use in interleaved diffusion MR imaging of an anatomical volume, according to an embodiment of the invention.

FIG. 12 shows a flowchart of a process performed by system 10 (FIG. 1) for determining motion correction data for use in interleaved diffusion MR imaging of an anatomical volume. In step 852 following the start at step 851 an RF (Radio Frequency) signal generator 4 generates RF excitation pulses in an anatomical volume (region) of interest and enables subsequent acquisition of associated RF echo data. In step 855 magnetic field gradient generator 3 generates anatomical slice specific magnetic field gradients for phase encoding and readout RF data acquisition. RF signal generator 4 and gradient generator 3 in step 857 sequentially acquire in a single first direction through the volume, first and second slice sets individually comprising multiple individual diffusion image slices by providing a first pulse sequence for acquiring the second slice set. The first set of slices and the second set of slices are spatially interleaved within the volume.

The first pulse sequence comprises a low flip angle RF pulse successively followed by a non-diffusion image data readout magnetic field gradient for acquisition of data representing a two dimensional (2D) non-diffusion image used for motion detection of the first slice set successively followed by, a first diffusion imaging RF pulse followed by a first diffusion imaging phase encoding magnetic field gradient for preparation for acquiring data representing a diffusion image slice of the second slice set. The first diffusion imaging phase encoding magnetic field gradient is successively followed by a second diffusion imaging RF pulse followed by a second diffusion imaging phase encoding magnetic field gradient, followed by a diffusion image data readout magnetic field gradient for acquisition of the data representing the diffusion image slice. The low flip angle substantially comprises a 5-30 degree angle, the first diffusion imaging RF pulse is substantially a 90 degree pulse and the second diffusion imaging RF pulse is substantially a 180 degree pulse. In one embodiment the diffusion image data readout magnetic field gradient is an echo planar imaging diffusion image data readout magnetic field gradient.

The first diffusion imaging phase encoding magnetic field gradient occurs substantially within half the Echo Time (TE) used in acquiring the diffusion image slice of the second slice set and the second diffusion imaging phase encoding magnetic field gradient and the echo planar diffusion image data readout magnetic field gradient occur substantially within half the Echo Time (TE) used in acquiring the diffusion image slice of the second slice set. The system acquires data representing the diffusion image slice of the second slice set using one of multiple different diffusion acquisition methods including, (a) Stejskal-Tanner, (b) twice refocused methods, (c) stimulated echo (d) q-space (e) diffusion spectrum imaging and (f) diffusion tensor imaging, methods, for example. The RF signal generator and the gradient generator provides, in acquiring the first slice set, a low flip angle RF pulse successively followed by a non-diffusion image data readout magnetic field gradient for acquisition of data representing a two dimensional (2D) non-diffusion image used for motion detection of the second slice set successively followed by, a first diffusion imaging RF pulse followed by a first diffusion imaging phase encoding magnetic field gradient for preparation for acquiring data representing a diffusion image slice of the first slice set. In one embodiment, the low flip angle RF pulse is followed by the non-diffusion image data readout magnetic field gradient without intervening pulses. Further, the non-diffusion image data readout magnetic field gradient is followed by the first diffusion imaging RF pulse without intervening pulses and the first diffusion imaging RF pulse is followed by the first diffusion imaging phase encoding magnetic field gradient without intervening pulses.

In step 859, system 10 acquires a two dimensional (2D) non-diffusion image in a single second direction different to the first direction. An image data processor in imaging computer 17 (FIG. 1) in step 863 compares multiple two dimensional (2D) non-diffusion images comprising a set of images in the single first and second directions to detect movement of an object between compared non-diffusion images. The image data processor uses the detected movement of the object to correct the three dimensional spatial coordinates of a diffusion image slice acquired in the single second direction relative to a diffusion image slice acquired in the single first direction to compensate for the detected movement. The process of FIG. 12 terminates at step 881.

Figure 13:
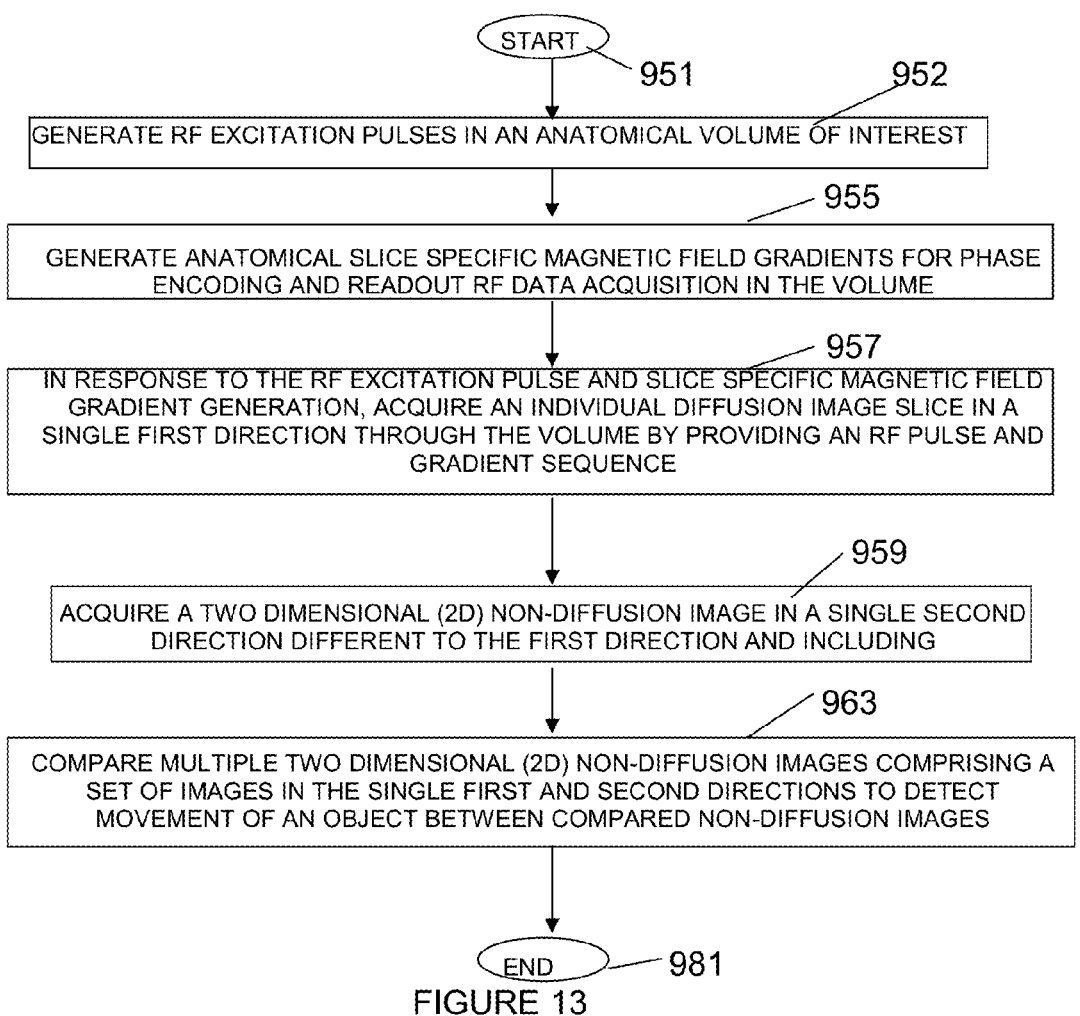
FIG. 13 shows a flowchart of a process performed by a system for determining motion correction data for use in integrated diffusion MR imaging of an anatomical volume, according to an embodiment of the invention.

FIG. 13 shows a flowchart of a process performed by a system for determining motion correction data for use in integrated diffusion MR imaging of an anatomical volume. In step 952 following the start at step 951 an RF (Radio Frequency) signal generator 4 generates RF excitation pulses in an anatomical volume (region) of interest and enables subsequent acquisition of associated RF echo data. In step 955 magnetic field gradient generator 3 generates anatomical slice specific magnetic field gradients for phase encoding and readout RF data acquisition. RF signal generator 4 and gradient generator 3 in step 957 acquire an individual diffusion image slice in a single first direction through the volume by providing a second pulse sequence.

The second pulse sequence comprises a first diffusion imaging RF pulse, a non-diffusion image data readout magnetic field gradient for acquisition of data representing a two dimensional (2D) non-diffusion image used for motion detection and a first diffusion imaging phase encoding magnetic field gradient for magnetic preparation for acquiring data representing the individual diffusion image slice. The second pulse sequence further comprises a subsequent second diffusion imaging RF pulse, a second diffusion imaging phase encoding magnetic field gradient and a diffusion image data readout magnetic field gradient for acquisition of data representing the individual diffusion image slice. In one embodiment, following the second diffusion imaging RF pulse and prior to the second diffusion imaging phase encoding magnetic field gradient, the second pulse sequence incorporates a time delay to correct an Echo Time (TE) value.

In one embodiment, the first diffusion imaging RF pulse is substantially a 90 degree pulse and the second diffusion imaging RF pulse is substantially a 180 degree pulse. Further, the first diffusion imaging phase encoding magnetic field gradient occurs substantially within half the Echo Time (TE) used in acquiring the individual diffusion image slice and the second diffusion imaging phase encoding magnetic field gradient and the echo planar imaging diffusion image data readout magnetic field gradient occur substantially within half the Echo Time (TE) used in acquiring the individual diffusion image slice. In one embodiment, the diffusion image data readout magnetic field gradient is an echo planar imaging diffusion image data readout magnetic field gradient. The system acquires data representing the diffusion image slice using one of multiple different diffusion acquisition methods including, (a) Stejskal-Tanner, (b) twice refocused methods, (c) stimulated echo (d) q-space (e) diffusion spectrum imaging and (f) diffusion tensor imaging, methods, for example.

In step 959, system 10 acquires a two dimensional (2D) non-diffusion image in a single second direction different to the first direction. An image data processor in imaging computer 17 (FIG. 1) in step 963 compares multiple two dimensional (2D) non-diffusion images comprising a set of images in the single first and second directions to detect movement of an object between compared non-diffusion images. The image data processor uses the detected movement of the object to correct the three dimensional spatial coordinates of a diffusion image slice acquired in the single second direction relative to a diffusion image slice acquired in the single first direction to compensate for the detected movement. The process of FIG. 13 terminates at step 981.

Returning to FIG. 1, RF coils 4 emit RF pulses to excite nuclear proton spins in a patient on support table 5 in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via a radio-frequency amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

Definitions

EPI comprises Echo planar imaging involves image acquisition whereby a complete image is formed from a single data sample (k-space lines are acquired in one repetition time) of a gradient echo or spin echo sequence.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI comprises inversion time, the time between an inversion recovery pulse and the next RF excitation pulse. TI determines the image contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

$TR_{ALL}$ comprises a total repetition time comprising multiple individual TR repetition times between successive RF excitation pulses for acquiring a predetermined total number of slices in a diffusion imaging direction using a particular diffusion encoding method.

TE (Echo Time) comprises a time period between the start of an RF pulse and the maximum in the received echo signal. The sequence is repeated every TR seconds.

B0 is the main static base MRI magnetic field.

B1 is the RF transmit coil field.

b-value comprises a factor of diffusion weighted sequences summarizing the influence of gradients on diffusion weighted images, the higher the value b, the stronger the diffusion weighting increased sensitivity to diffusion.

The system and processes of FIGS. 1-13 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system provides prospective motion correction for 2D multislice diffusion imaging, by using non-diffusion encoded low resolution single shot EPI images as motion navigators (EPI Navigator images) during a diffusion scan in different interleaved and integrated diffusion imaging embodiments. Further, the processes and applications may, in alternative embodiments, be located on one or more (e.g., distributed) processing devices on a network linking the units of FIG. 1. Any of the functions and steps provided in FIGS. 1-13 may be implemented in hardware, software or a combination of both.

What is claimed is:

1. A system for determining motion correction data for use in diffusion MR imaging of an anatomical volume, comprising:
   an RF (Radio Frequency) signal generator configured to generate RF excitation pulses in an anatomical region of interest to facilitate subsequent acquisition of associated RF echo data; and
   a magnetic field gradient generator configured to generate anatomical slice specific magnetic field gradients for phase encoding and readout RF data acquisition,
   wherein said RF signal generator and said gradient generator are configured to sequentially acquire a first slice set and a second slice sets in a single first direction through said volume,
   wherein each of the first slice set and the second slice set comprises a plurality of individual diffusion image slices,
   wherein the slices of the first slice set are spatially interleaved with the slices of the second slice set within said volume, and
   wherein said RF signal generator and said gradient generator are further configured to acquire said second slice set by providing, a low flip angle RF pulse successively followed by:
      a non-diffusion image data readout magnetic field gradient for to facilitate acquisition of data representing a two-dimensional (2D) non-diffusion image used for motion detection of the first slice set,
      a first diffusion imaging RF pulse, and
      a first diffusion imaging phase encoding magnetic field gradient for magnetic preparation to facilitate acquisition of data representing a diffusion image slice of the second slice set.

2. A system according to claim 1, wherein
   said RF signal generator and said gradient generator are configured to provide, in acquiring said first slice set, a low flip angle RF pulse successively followed by:
      a non-diffusion image data readout magnetic field gradient to facilitate acquisition of data representing a two dimensional (2D) non-diffusion image used for motion detection of the second slice set,
      a first diffusion imaging RF pulse, and
      a first diffusion imaging phase encoding magnetic field gradient,
   to facilitate acquisition of data representing a diffusion image slice of the first slice set.

3. A system according to claim 2, wherein said first diffusion imaging phase encoding magnetic field gradient is successively followed by:
   a second diffusion imaging RF pulse,
   a second diffusion imaging phase encoding magnetic field gradient, and
   a diffusion image data readout magnetic field gradient,
to facilitate acquisition of said data representing said diffusion image slice.

4. A system according to claim 3, wherein
   said low flip angle comprises a 5-30 degree angle,
   said first diffusion imaging RF pulse is a 90 degree pulse, and
   said second diffusion imaging RF pulse is a 180 degree pulse.

5. A system according to claim 4, wherein
   said first diffusion imaging phase encoding magnetic field gradient occurs within half the Echo Time (TE) used in acquiring said diffusion image slice of the second slice set, and
   said second diffusion imaging phase encoding magnetic field gradient and said echo planar imaging diffusion image data readout magnetic field gradient occur within half the Echo Time (TE) used in acquiring said diffusion image slice of the second slice set.

6. A system according to claim 1, wherein
   said first diffusion imaging phase encoding magnetic field gradient occurs within half the Echo Time (TE) used in acquiring said diffusion image slice of the second slice set.

7. A system according to claim 1, wherein
   said low flip angle RF pulse is followed by said non-diffusion image data readout magnetic field gradient without any intervening pulses,
   said non-diffusion image data readout magnetic field gradient is followed by said first diffusion imaging RF pulse without any intervening pulses, and
   said first diffusion imaging RF pulse is followed by said first diffusion imaging phase encoding magnetic field gradient without any intervening pulses.

8. A system according to claim 1, wherein said system is configured to acquire a two dimensional (2D) non-diffusion image in a single second direction that is different than said first direction, and
   wherein said system further comprises an image data processor configured to compare a plurality of two dimensional (2D) non-diffusion images comprising a set of images in each of the single first and second directions to detect a movement of an object between the compared non-diffusion images.

9. A system according to claim 8, wherein
   said image data processor is further configured to correct the three dimensional spatial coordinates of a diffusion image slice acquired in said single second direction relative to a diffusion image slice acquired in said single first direction, based on the detected movement of said object, to compensate for said detected movement.

10. A system according to claim 3, wherein
    said diffusion image data readout magnetic field gradient is an echo planar imaging diffusion image data readout magnetic field gradient.

11. A system according to claim 1, wherein
    said system is configured to acquire data representing said diffusion image slice of the second slice set using one of a plurality of different diffusion acquisition techniques.

12. A system according to claim 11, wherein
said plurality of diffusion acquisition techniques includes at least one of: (a) a Stejskal-Tanner technique, (b) a twice refocused technique, (c) a stimulated echo technique, (d) q-space technique, (e) a diffusion spectrum imaging technique, and (f) a diffusion tensor imaging technique.

13. A method for determining motion correction data for use in diffusion MR imaging of an anatomical volume, comprising the steps of:
generating RF excitation pulses in an anatomical volume of interest;
generating anatomical slice: specific magnetic field gradients for phase encoding and readout RF data acquisition in said volume; and
in response to the RF excitation pulse and slice: specific magnetic field gradient generation, sequentially acquiring a first slice set and a second slice sets in a single first direction through said volume, by providing in acquiring said second slice set a low flip angle RF pulse successively followed by:
a non-diffusion image data readout magnetic field gradient adapted to facilitate acquisition of data representing a two dimensional (2D) non-diffusion image used for motion detection of the first slice set,
a first diffusion imaging RF pulse, and
a first diffusion imaging phase encoding magnetic field gradient adapted to provide magnetic preparation to facilitate acquisition of data representing a diffusion image slice of the second slice set,
wherein each of said first and second slice sets comprises a plurality of individual diffusion image slices, and
wherein the first set of slices and the second set of slices are spatially interleaved within said volume.

* * * * *